US00PP22009P2

(12) United States Plant Patent
Herrera Valenzuela et al.

(10) Patent No.: US PP22,009 P2
(45) Date of Patent: Jul. 5, 2011

(54) ***ALSTROEMERIA* PLANT NAMED 'JASOA'**

(50) Latin Name: *Alstroemeria hybrida*
Varietal Denomination: Jasoa

(75) Inventors: Camilo Herrera Valenzuela, Bogotá (CO); Henry Belalcázar Valencia, Bogotá (CO)

(73) Assignee: C.I. Valmar S.A., Bogotá (CO)

( * ) Notice: Subject to any disclaimer, the term of this patent is extended or adjusted under 35 U.S.C. 154(b) by 0 days.

(21) Appl. No.: 12/660,118

(22) Filed: Feb. 19, 2010

(51) Int. Cl.
*A01H 5/00* (2006.01)

(52) U.S. Cl. ..... Plt./309

(58) Field of Classification Search ..... Plt./309
See application file for complete search history.

*Primary Examiner* — June Hwu
(74) *Attorney, Agent, or Firm* — C. A. Whealy

(57) ABSTRACT

A new and distinct cultivar of *Alstroemeria* plant named 'Jasoa', characterized by its erect and strong flowering stems; vigorous growth habit; large yellow and orange-colored flowers with dark red purple-colored flecks and streaks, flowers arranged in symmetrical umbels; and excellent postproduction longevity.

1 Drawing Sheet

Botanical designation: *Alstroemeria hybrida.*
Cultivar denomination: 'JASOA'.

BACKGROUND OF THE INVENTION

The present invention relates to a new and distinct cultivar of *Alstroemeria* plant, botanically known as *Alstroemeria hybrida,* commercially used as a cut flower *Alstroemeria,* and hereinafter referred to by the name 'Jasoa'.

The new *Alstroemeria* plant is a product of a planned breeding program conducted by the Inventors in Madrid, Cundinamarca, Colombia. The objective of the breeding program was to create new *Alstroemeria* cultivars with desirable plant qualities, attractive flower color and excellent postproduction longevity.

The new *Alstroemeria* plant originated from a cross-pollination conducted in January, 2004 by the Inventors in Madrid, Cundinamarca, Colombia of a proprietary selection of *Alstroemeria hybrida* identified as code number JAH 116, not patented, as the female, or seed, parent with a proprietary selection of *Alstroemeria hybrida* identified as code number HH 711, as the male, or seed, parent. The new *Alstroemeria* plant was discovered and selected by the Inventors as a single flowering plant from within the progeny of the stated cross-pollination grown in a controlled greenhouse environment in Madrid, Cundinamarca, Colombia in May, 2005.

Asexual reproduction of the new *Alstroemeria* plant by rhizome divisions in a controlled greenhouse environment in Madrid, Cundinamarca, Colombia since July, 2005, has shown that the unique features of this new *Alstroemeria* plant are stable and reproduced true to type in successive generations.

SUMMARY OF THE INVENTION

Plants of the new *Alstroemeria* have not been observed under all possible environmental and cultural conditions. The phenotype may vary somewhat with variations in environment and cultural practices such as temperature and light intensity without, however, any variance in genotype.

The following traits have been repeatedly observed and are determined to be the unique characteristics of 'Jasoa'. These characteristics in combination distinguish 'Jasoa' as a new and distinct cultivar of *Alstroemeria* plant:

1. Erect and strong flowering stems.
2. Vigorous growth habit.
3. Large yellow and orange-colored flowers with dark red purple-colored flecks and streaks, flowers arranged in symmetrical umbels.
4. Excellent postproduction longevity.

Plants of the new *Alstroemeria* can be compared to plants of the parent selections. Plants of the new *Alstroemeria* differ from plants of the parent selections primarily in flower color as plants of the female parent selection have yellow-colored flowers and plants of the male parent selection have orange-colored flowers.

Plants of the new *Alstroemeria* can be compared to plants of *Alstroemeria hybrida* 'Stalove' disclosed in U.S. Plant Pat. No. 8,739. In side-by-side comparisons plants of the new *Alstroemeria* differed primarily from plants of 'Stalove' in the following characteristics:

1. Plants of the new *Alstroemeria* had larger inflorescences than plants of 'Stalove'.
2. Plants of the new *Alstroemeria* had more flowers per inflorescence than plants of 'Stalove'.
3. Plants of the new *Alstroemeria* had larger flowers with larger perianth segments than plants of 'Stalove'.
4. Plants of the new *Alstroemeria* and 'Stalove' differed slightly in flower color.
5. Plants of the new *Alstroemeria* had longer pedicels than plants of 'Stalove'.
6. Plants of the new *Alstroemeria* and 'Stalove' differed in anther color.
7. Plants of the new *Alstroemeria* and 'Stalove' differed in style, stigma and ovary color.

BRIEF DESCRIPTION OF THE PHOTOGRAPHS

The accompanying colored photographs illustrate the overall appearance of the new *Alstroemeria* plant, showing the colors as true as it is reasonably possible to obtain in colored reproductions of this type. Colors in the photographs may differ slightly from the color values cited in the detailed botanical description which accurately describe the colors of the new *Alstroemeria* plant.

The photograph at the bottom of the sheet comprises a side perspective view of a typical flowering stem of 'Jasoa'.

The photograph at the top of the sheet is a close-up view of a typical inflorescence of 'Jasoa'.

DETAILED BOTANICAL DESCRIPTION

The aforementioned photographs and following observations and measurements describe plants of the new *Alstroemeria* grown in Madrid, Cundinamarca, Colombia in a polyethylene-covered greenhouse in ground beds. During the production of the plants, maximum day temperatures averaged 31.5° C., maximum night temperatures averaged 6° C. and light levels averaged 21.4 KWH/m$^2$. Plants used for the photographs and description were four years old. Color references are made to The Royal Horticultural Society Colour Chart, 2007 Edition, except where general terms of ordinary dictionary significance are used.

Botanical classification: *Alstroemeria hybrida* 'Jasoa'.

Parentage:

*Female, or seed, parent.*—Proprietary selection of *Alstroemeria hybrida* identified as code number JAH 116, not patented.

*Male, or pollen, parent.*—Proprietary selection of *Alstroemeria hybrida* identified as code number HH 711.

Propagation:

*Type.*—By rhizome divisions.

*Time to initiate roots.*—About two weeks at temperatures ranging from about 6° C. to 32° C.

*Time to produce a rooted young plant.*—About eight weeks at temperatures ranging from about 6° C. to 32° C.

*Root description.*—Fleshy, medium in thickness; close to 155A in color.

*Rooting habit.*—Freely branching; dense.

*Rhizomes.*—Shape: Rounded. Length: About 4 cm. Diameter: About 1.17 cm. Texture: Fleshy. Color: Close to NN155A.

Plant description:

*Plant and growth habit.*—Upright; freely branching, bushy appearance; vigorous growth habit.

*Time from planting to harvest of cut flowers.*—About 19 weeks.

Flowering stem description:

*Aspect.*—Erect.

*Length.*—About 160 cm to 178 cm.

*Diameter.*—About 6 mm.

*Internode length.*—About 2.7 cm.

*Strength.*—Strong.

*Texture.*—Smooth, glabrous.

*Color.*—Close to 146B.

Foliage description:

*Arrangement.*—Alternate, simple.

*Length.*—About 14.5 cm.

*Width.*—About 3.2 cm.

*Shape.*—Oblanceolate.

*Apex.*—Acute.

*Base.*—Attenuate.

*Margin.*—Entire.

*Texture, upper and lower surfaces.*—Smooth, glabrous; longitudinally ridged.

*Venation pattern.*—Parallel.

*Color.*—Developing leaves, upper and lower surfaces: Close to 146B. Fully expanded leaves, upper and lower surfaces: Close to 146C; venation, close to 146B.

*Petioles.*—Length: About 2.4 cm. Diameter: About 5 mm. Texture, upper and lower surfaces: Smooth, glabrous. Color, upper and lower surfaces: Close to 144B.

Flower description:

*Flower type and arrangement.*—Single cup-shaped flowers arranged in compound umbels; flowers face upright to outwardly; perianth segments separate.

*Flowering habit.*—Freely flowering with about 15 to 20 open flowers and flower buds per inflorescence.

*Natural flowering season.*—Flowering continuous year round in a greenhouse in Colombia; plants begin flowering about 19 weeks after planting.

*Fragrance.*—None detected.

*Flower longevity as a cut flower.*—About two weeks; flowers not persistent.

*Flower buds (showing color).*—Length: About 4.2 cm. Diameter: About 1.5 cm. Shape: Obovate. Color: Close to 2D; apices, close to 144A.

*Umbel height.*—About 22 cm.

*Umbel diameter.*—About 17 cm by 20 cm.

*Flower diameter.*—About 7.5 cm.

*Flower length (height).*—About 7 cm.

*Flower depth.*—About 7 cm.

*Perianth.*—Arrangement: Six arranged in two whorls, each whorl with two lateral and one median segments. Inner perianth, lateral segments: Length: About 6.8 cm. Width: About 2.2 cm. Shape: Oblanceolate. Apex: Acute to mucronate. Base: Attenuate. Margin: Entire; towards the apex, slightly erose. Texture, upper and lower surfaces: Smooth, glabrous; satiny. Color, when opening, upper surface: Towards the apex, close to 4C; mid-section, close to 9A; towards the base, close to 4C; flecks and streaks, close to 59B. Color, when opening, lower surface: Towards the apex, close to 4C; mid-section, close to 9C; towards the base, close to 4C. Color, fully opened, upper surface: Close to 9A; towards the base, close to 9C; flecks and streaks, close to 59B; with development, color becomes closer to 21B and flecks and streaks, close to 53A. Color, fully opened, lower surface: Close to 9B; towards the base, close to 9C. Inner perianth, median segment: Length: About 5.8 cm. Width: About 2.2 cm. Shape: Oblanceolate. Apex: Acute to mucronate. Base: Attenuate. Margin: Entire; towards the apex, slightly erose. Texture, upper and lower surfaces: Smooth, glabrous; satiny. Color, when opening, upper surface: Towards the apex, close to 4C to 4D; mid-section, close to 9C; towards the base, close to 4C to 4D. Color, when opening, lower surface: Close to 11B. Color, fully opened, upper surface: Close to 9C to 9D; flecks and streaks, close to 59B; with development, color becomes closer to 21 B and flecks and streaks, close to 53A. Color, fully opened, lower surface: Close to 11B. Outer perianth, lateral segments: Length: About 5.9 cm. Width: About 3.4 cm. Shape: Obovate to cordate. Apex: Cordate. Base: Attenuate. Margin: Entire. Texture, upper and lower surfaces: Smooth, glabrous; satiny. Color, when opening, upper surface: Close to 11B; towards the base, close to 11C to 11D. Color, when opening, lower surface: Close to 11B to 11C; venation, close to 144A. Color, fully opened, upper surface: Close to 13A; towards the base, close to 9D; with development color becomes closer to 21B to 21C. Color, fully opened, lower surface: Close to 13C to 13D. Outer perianth, median segment: Length: About 6.3 cm. Width: About 3.4 cm. Shape: Obovate to cordate. Apex: Cordate. Base: Attenuate. Margin: Entire. Texture, upper and lower surfaces: Smooth, glabrous; satiny. Color, when opening, upper surface: Towards the apex, close to 11B; mid-section, close to 9C; towards the base, close to 11B. Color, when opening, lower surface: Close to 11B; venation, close to 144A. Color, fully opened, upper surface: Close to 13A; towards the base, close to 9D; with development color becomes closer to 21B to 21C. Color, fully opened, lower surface: Close to 11B; towards the base, close to 11C.

*Pedicels.*—Length: About 6 cm. Diameter: About 2 mm. Strength: Strong. Angle: About 15° to 25° from the peduncle axis. Texture: Smooth, glabrous. Color: Close to 144B.

*Reproductive organs.*—Stamens: Quantity per flower: Six. Anther shape: Elongated. Anther length: About 7 mm. Anther diameter: About 2 mm. Anther color: Close to 152C. Pollen amount: Moderate. Pollen color: Close to 14A. Pistils: Quantity per flower: One. Pistil length: About 5.6 cm. Style length: About 4.5 cm. Style color: Close to 12C to 12D. Stigma shape: Three-parted. Stigma color: Close to 12A. Ovary color: Close to 146C.

*Fruit/seed.*—Fruit and seed development has not been observed.

Disease/pest resistance: Plants of the new *Alstroemeria* have not been observed to be resistant to pathogens and pests common to *Alstroemeria*.

It is claimed:

1. A new and distinct *Alstroemeria* plant named 'Jasoa' as illustrated and described.

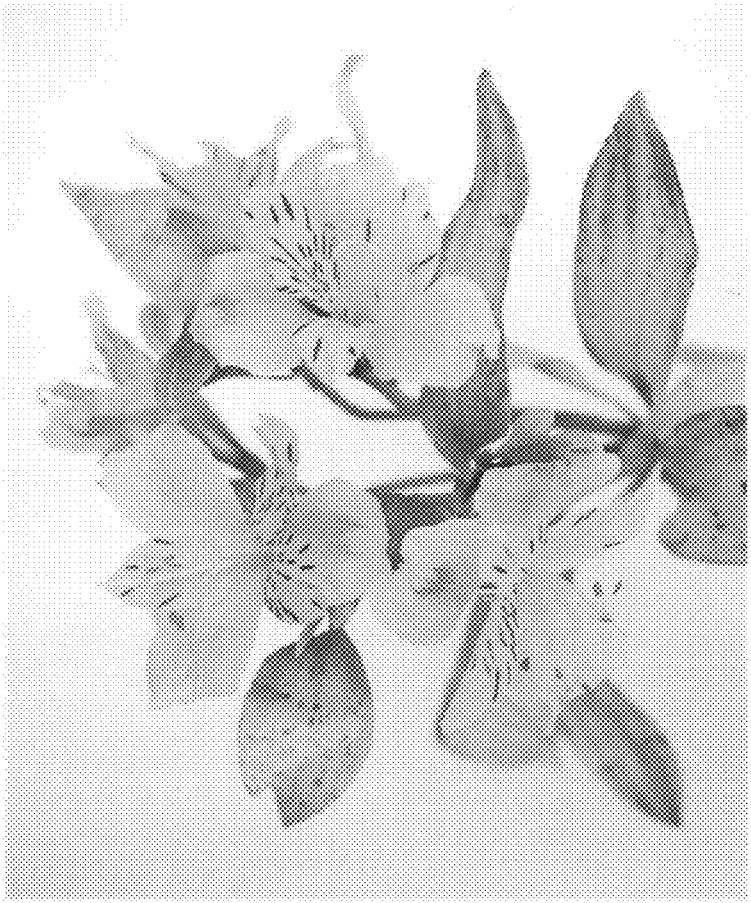
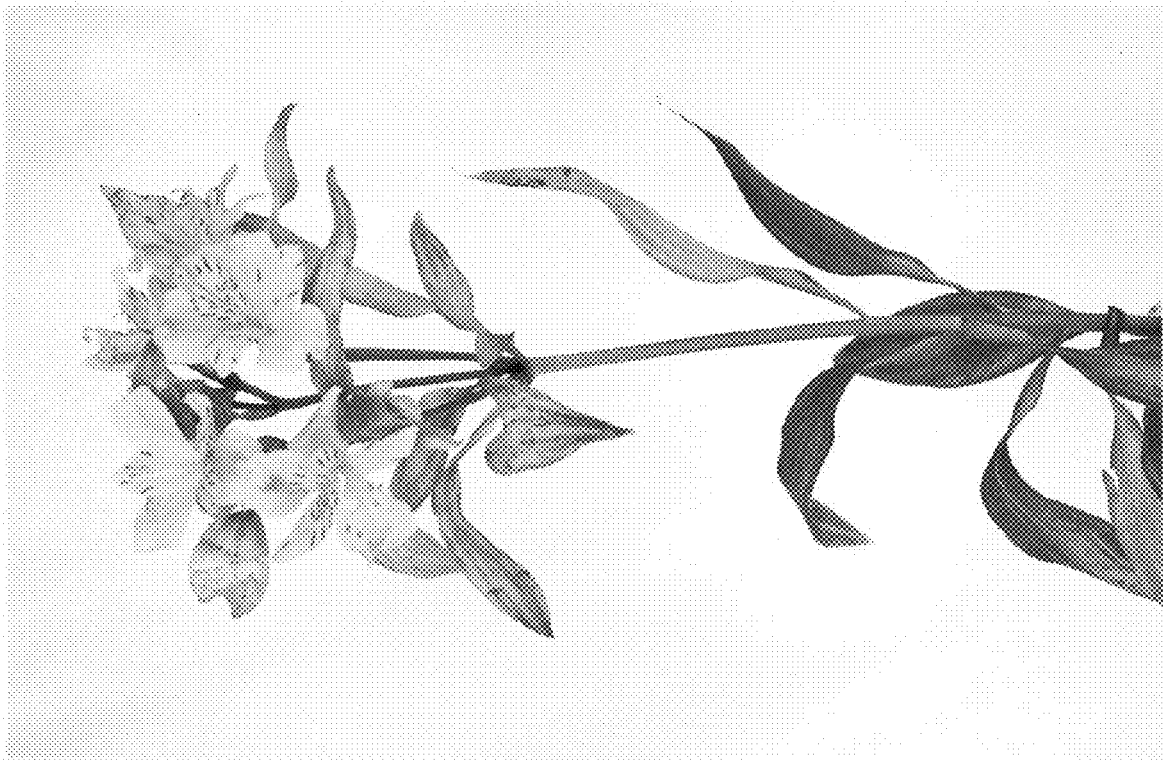

* * * * *